United States Patent [19] [11] 4,164,504
Varma [45] Aug. 14, 1979

[54] STEROIDAL[16α,17-b]NAPHTHALENO-21-CARBOXYLIC ACID ESTERS

[75] Inventor: Ravi K. Varma, Belle Mead, N.J.

[73] Assignee: E. R. Squibb & Sons, Inc., Princeton, N.J.

[21] Appl. No.: 919,020

[22] Filed: Jun. 26, 1978

[51] Int. Cl.² .............................................. C07J 5/00
[52] U.S. Cl. ............................ 260/397.1; 260/397.45
[58] Field of Search ...................................... 260/397.1

[56] References Cited
U.S. PATENT DOCUMENTS

| | | | |
|---|---|---|---|
| 3,919,421 | 11/1975 | Laurent et al. | 260/397.1 |
| 3,937,720 | 2/1976 | Varma et al. | 260/397.45 |

Primary Examiner—Elbert L. Roberts
Attorney, Agent, or Firm—Lawrence S. Levinson; Donald J. Barrack

[57] ABSTRACT

Steroids having the formula

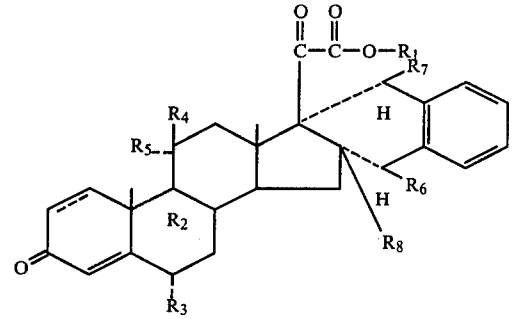

wherein $R_1$ is alkyl, aryl, or arylalkyl; $R_2$ is hydrogen or halogen; $R_3$ is hydrogen, methyl or fluorine; $R_4$ is chlorine, fluorine or hydroxy and $R_5$ is hydrogen or $R_4$ and $R_5$ together are =O; $R_6$ and $R_7$ are the same or different and are hydrogen, alkyl, alkoxy, carboalkoxy, formyl,

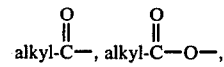

hydroxy, halogen, phenyl or cyano with the proviso that when $R_6$ and $R_7$ are different, one of $R_6$ and $R_7$ is hydrogen; $R_8$ is hydrogen or

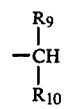

wherein $R_9$ and $R_{10}$ are the same or different and are hydrogen or alkyl have useful antiinflammatory activity.

19 Claims, No Drawings

STEROIDAL[16α,17-b]NAPHTHALENO-21-CARBOXYLIC ACID ESTERS

BACKGROUND OF THE INVENTION

Antiinflammatory activity, topical and systemic, is exhibited by many steroids of the pregnene series. More specifically, steroidal[16α,17-b]naphthalenes having the formula

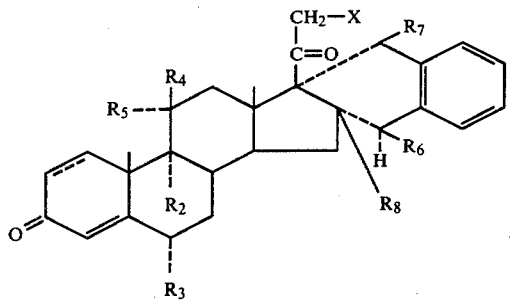

wherein X is hydrogen, hydroxy, acyloxy or halogen, and the "R groups" are as defined hereinafter, are disclosed as having topical and systemic antiinflammatory activity; see, for example, U.S. Pat. Nos. 3,937,720 issued Feb. 10, 1976 and 3,994,935 issued Nov. 30, 1976.

The prior art also discloses various pregnene-21-oic acid derivatives and corresponding esters as having topical antiinflammatory activity, while being essentially inactive systemically. Exemplary disclosures are U.S. Pat. Nos. 3,956,347 issued May 11, 1976; 3,919,421 issued Nov. 11, 1975; 4,049,804, issued Sept. 30, 1977; and Laurent et al., *Journal of Steroid Biochemistry*, 6: 185–192 (1975). One such pregnene derivative, fluocortin butyl ester (6α-fluoro-11β-hydroxy-16α-methyl-3,20-dioxopregna-1,4-diene-21-oic acid, butyl ester) has drawn particular attention and interest. Monder et al., *Journal of Steroid Biochemistry*, 8:897–908 (1977), discuss the synthesis of carboxylic acid derivatives of steroids, and the existense of these derivatives as metabolites of steroids.

SUMMARY OF THE INVENTION

Steroids having the formula I

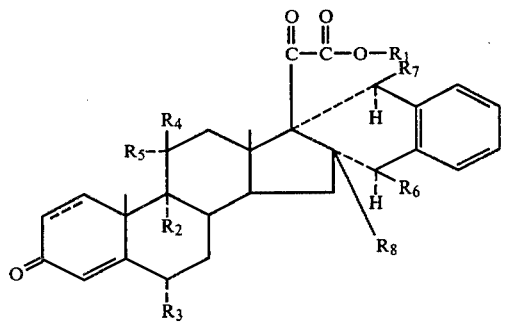

are useful as topical antiinflammatory agents. In formula I, and throughout the specification, the symbols are as defined below:

$R_1$ is alkyl of 1 to 10 carbon atoms, aryl, or arylalkyl;
$R_2$ is hydrogen or halogen;
$R_3$ is hydrogen, fluorine or methyl;
$R_4$ is chlorine, fluorine or hydroxy and $R_5$ is hydrogen or $R_4$ and $R_5$ together are =O;
$R_6$ and $R_7$ are the same or different and are hydrogen, alkyl, alkoxy, carboalkoxy, formyl,

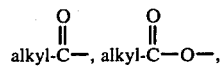

hydroxy, halogen, phenyl or cyano with the proviso that when $R_6$ and $R_7$ are different, one of $R_6$ and $R_7$ is hydrogen; and $R_8$ is hydrogen or

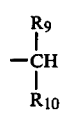

wherein $R_9$ and $R_{10}$ are the same or different and are hydrogen or alkyl.

The dotted lines in the 1,2-position of the steroids of this invention represent the optional presence of ethylenic unsaturation.

The terms "alkyl" and "alkoxy", as used throughout the specification (unless otherwise defined), refer to both straight and branched chain groups having 1 to 6 carbon atoms.

The term "aryl", as used throughout the specification, refers to phenyl or phenyl substituted with one or more halogen, alkyl and alkoxy groups.

The term "halogen", as used throughout the specification, refers to fluorine, chlorine, bromine and iodine.

DETAILED DESCRIPTION OF THE INVENTION

The steroids of formula I can be prepared from the corresponding 21-hydroxy-steroidal[16α,17-b]naphthalene having the structural formula II

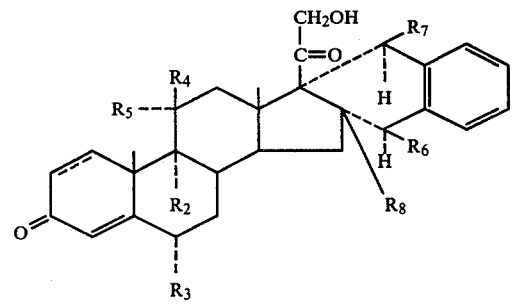

The steroids of formula II are known in the art; see, for example, U.S. Pat. Nos. 3,927,720 issued Feb. 10, 1976 and 3,994,935 issued Nov. 30, 1976.

A steroid of formula II can be oxidized to the corresponding aldehyde having the formula III

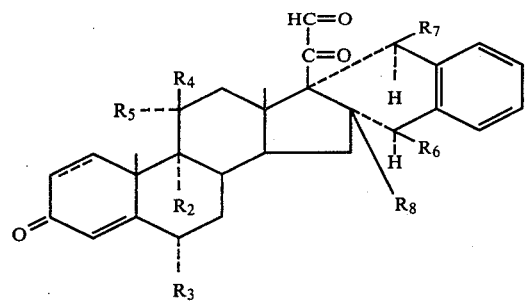

using a catalyst such as copper acetate. The reaction can be run in an alcohol solvent.

If the above described oxidation reaction is carried out in the presence of oxygen (e.g., by bubbling air through the reaction mixture), the reaction will generally yield, in addition to a steroidal-21-aldehyde of formula III, the corresponding steroidal-21-acetal formed with the alcohol solvent ($R_1$—OH); i.e., a steroid having the formula IV

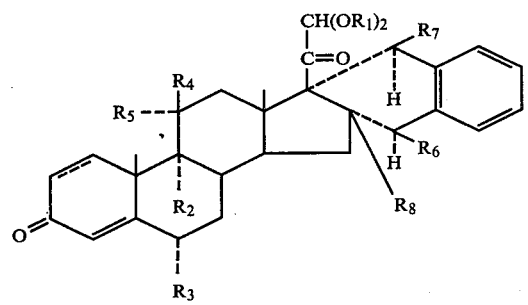

The oxidation reaction will generally be completed within a relatively short period of time, i.e., about 1 hour.

If the above-described reaction is allowed to proceed for an extended period of time, e.g., more than about 24 hours, the major product will be the 20-hydroxy-21-carboxylic acid ester having the formula V

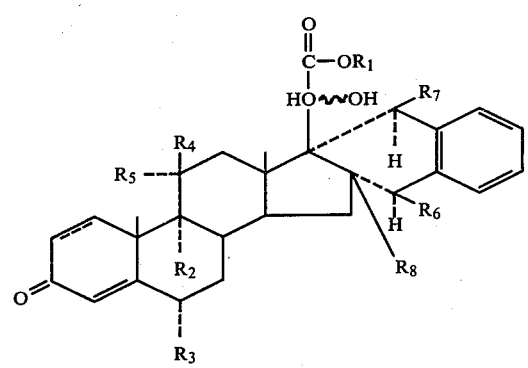

If water is present as a co-solvent in the oxidation reaction, and the reaction is allowed to proceed for an extended period of time, in addition to the 20-hydroxy-21-carboxylic acid ester of formula V, the corresponding 20-hydroxy-21-carboxylic acid will be produced; i.e., a steroid having the formula VI

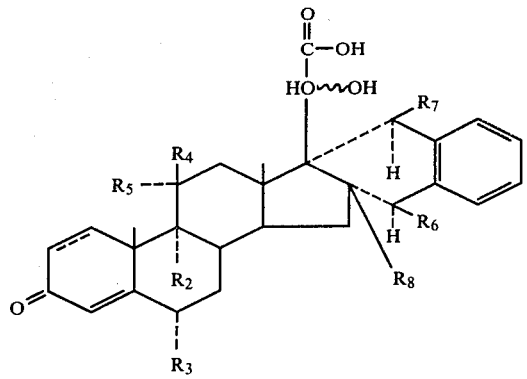

The steroids of formulas V and VI exist as mixtures of the 20α- and 20β-hydroxysteroids.

A product of formula I can be obtained by reacting a mixture of a steroidal-21-aldehyde of formula III and the corresponding steroidal-21-acetal of formula IV with a mixture of (i) an inorganic cyanide catalyst (e.g., an alkali metal cyanide such as potassium cyanide); (ii) an oxidizing agent, e.g., a heavy metal oxide such as activated manganese dioxide or lead dioxide, (iii) an inert solvent, e.g., a halogenated hydrocarbon solvent such as dichloromethane or chloroform; (iv) a primary or secondary alcohol, $R'_1$-OH (throughout the specification $R'_1$ is any primary or secondary $R_1$ group); and (v) an acid, e.g., acetic acid, which serves to neutralize the alkali cyanide catalyst. The products of the above reaction have the formula

VII

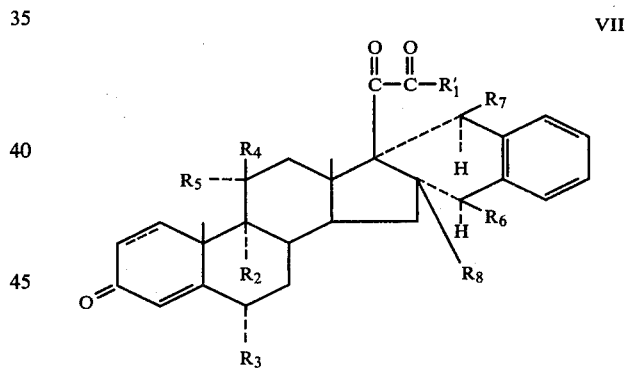

The 20α- and 20β-hydroxysteroids of formulas V and VI can be oxidized to obtain the corresponding 20-ketosteroids, having the respective formulas I

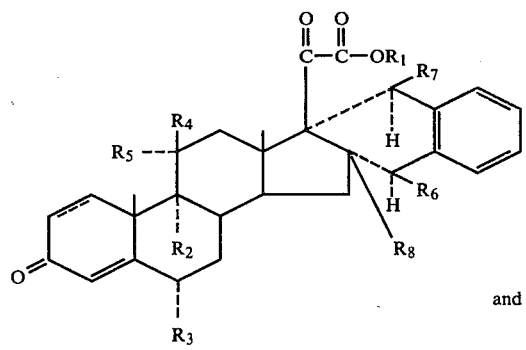

VIII and

-continued

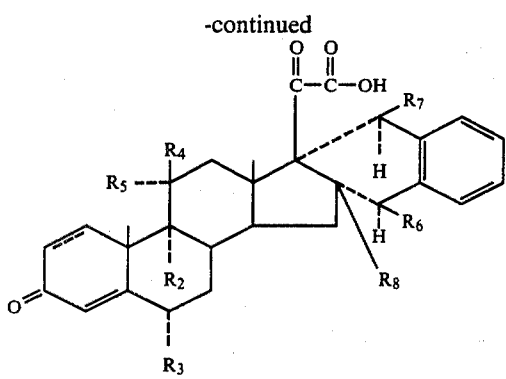

Exemplary of suitable oxidizing agents are manganese dioxide and chromium dioxide. In the instance wherein the 20α- and 20β-hydroxysteroids being oxidized have an 11β-hydroxy substituent, the products of formulas I and VIII will be mixtures of 11β-hydroxy and 11-keto steroids.

The products of formula I can also be prepared by esterification of the corresponding steroidal-21-oic acid of formula VIII. (A steroid of formula VIII can be prepared as described above, or alternatively, by saponification of a corresponding steroidal-21-oic acid ester of formula I.)

Still another route for the preparation of the products of formula I wherein $R_1$ is a non-tertiary alkyl group of 1 to 10 carbon atoms or aryl is the transesterification of another ester of formula I. The starting steroid is reacted with the appropriate alcohol in the presence of a basic alkoxide (e.g., sodium ethoxide or aluminum isopropoxide) or, preferably, a source of cyanide ion (e.g., an alkali metal cyanide such as sodium cyanide or potassium cyanide to yield the transesterification product.

The steroids of formula I are useful topical antiinflammatory agents which can be used in lieu of known glucocorticoids in the treatment of conditions such as dermatitis, psoriasis, sunburn, neurodermatitis, eczema and anogenital pruritus. The steroids may be administered in a conventional cream, ointment, lotion or spray in the range of 0.01 to 5.0% by weight, preferably 0.025 to 2.0% by weight.

The following examples are specific embodiments of this invention.

The steroids of formulas III, IV, V, VI and VIII are novel compounds that are useful in the preparation of the steroids of formula I; as such, they constitute an integral part of this invention.

EXAMPLE 1

9-Fluoro-1',2'3'4'-tetrahydro-11β-hydroxy-3,20-dioxopregna-1,4-dieno[16α,17-b]naphthalene-21-oic acid, methyl ester 9-Fluoro-1',2',3',4'-tetrahydro-11β,21-dihydroxypregna-1,4-dieno[16α,17-b]naphthalene-3,20-dione (1.0 g) is dissolved in anhydrous methanol (170 ml) by warming and the solution is cooled to room temperature. Cupric acetate hydrate (250 mg) is added and under stirring, a slow stream of air is passed into the solution. Within 10 minutes, the starting steroid disappears to give essentially a single less polar material, as judged by thin-layer chromatography (TLC). The methanol is mostly evaporated in vacuo at room temperature; some steroid precipitates out. The concentrate is diluted with water and extracted with chloroform. The chloroform solution is washed with a dilute ammonium chloride solution and water, dried over anhydrous magnesium sulfate and evaporated to leave 0.98 g of 9-fluoro-1',2',3',4'-tetrahydro-11β-hydroxypregna-1,4-dieno[16α,17-b] naphthalene-21-al-3,20-dione. This material shows a single spot on TLC (chloroform-methanol, 93:7; silica gel) and an IR spectrum consistent with the structure. However, the NMR spectrum shows that it is contaminated with a small amount of the corresponding 21-dimethyl acetal.

A mixture of the impure aldehyde (950 mg), anhydrous methanol (50 ml), dry dichloromethane (50 ml), glacial acetic acid (0.9 ml), potassium cyanide (200 mg) and active manganese dioxide (2.1 g) is stirred at room temperature for 10 hours. It is then filtered through a bed of diatomaceous earth. The cake is resuspended in chloroform which is refluxed and filtered again. The filtrates are combined, washed with a dilute sodium bicarbonate solution and water, dried over anhydrous magnesium sulfate and evaporated to afford 0.86 g of a solid. This is dissolved in a mixture of dichloromethane and methanol. The dichloromethane is removed under reflux to precipitate 675 mg of a solid. This is again subjected to purification as above to afford 630 mg of the title compound, melting point 319°–321° C. (dec., discoloration starts from about 260° C.) with consistent spectral data.

Anal. Calc'd for $C_{30}H_{33}FO_5$: C, 73.15; H, 6.75; F, 3.86 Found: C, 72.85; H, 6.95; F, 3.65.

EXAMPLE 2

9-Fluoro-1',2',3',4'-tetrahydro-11β-hydroxy-3,20-dioxopregna-1,4-dieno[16α,17-b]naphthalen-21-oic acid, 1-methylethyl ester A suspension of 9-fluoro-1',2',3',4'-tetrahydro-11β-hydroxy-3,20-dioxopregna-1,4-dieno[16α,17-b]naphthalen-21-oic acid, methyl ester (490 mg., see Example 1) in dry isopropanol (30 ml, freshly distilled from magnesium turnings) containing sodium cyanide (10 mg) is refluxed under an atmosphere of nitrogen for 20 minutes when a clear solution results. A TLC examination at this point shows complete conversion of the starting steroid into a less polar compound. The mixture is then evaporated in vacuo, the residue is dissolved in chloroform, washed with dilute brine and water, dried over anhydrous magnesium sulfate and evaporated to afford 516 mg of the title compound. One crystallization from ethyl acetate affords the analytical specimen of the title compound as colorless needles (410 mg), melting point 269°–271° C. (dec., discoloration starts from about 250° C.) with consistent spectral data.

Anal. Calc'd for $C_{32}H_{37}FO_5$: C, 73.82; H, 7.16; F, 3.65 Found: C, 73.45; H, 7.11; F, 3.47.

EXAMPLE 3

9-Fluoro-1',2',3',4'-tetrahydro-11β-hydroxy, 3,20-dioxopregna-1,4-dieno[16α,17-b]naphthalen-21-oic acid, butyl ester 9-Fluoro-1',2',3',4'-tetrahydro-11β,21-dihydroxypregna-1,4-dieno[16α,17-b]naphthalene-3,20-dione (800 mg) is dissolved in n-butanol (150 ml) by warming. The solution is cooled to room temperature, copper acetate hydrate (250 mg) is added and air is bubbled into the solution with stirring for 30 minutes. Most of the n-butanol is then removed by evaporation in vacuo at 40°–42° C. The concentrate is diluted with water and extracted with chloroform. The chloroform extracts are combined, washed with a dilute ammonium chloride solution and water, dried over anhydrous magnesium sulfate and evaporated to afford 850 mg of 9-fluoro-1',2',3',4'-tetrahydro-11β-hydroxypregna-1,4-dieno[1-6α,17-b]naphthalene-21-al-3,20-dione. (This material is characterized spectroscopically. A TLC examination shows the presence of one major compound, traces of starting material and traces of another impurity, less polar than the starting material, and believed to be 9-fluoro-1',2',3',4'-tetrahydro-11β-hydroxy-21,21-di-n-butoxy-pregna-1,4-dieno[16α,17-b]naphthalene-3,20-dione).

The above crude mixture (840 mg) is dissolved in a mixture of dry n-butanol (20 ml) and dichloromethane (50 ml). Acetic acid (0.8 ml), potassium cyanide (200 mg) and active manganese dioxide (2.0 g) are added and the mixture is stirred at room temperature for 60 hours. (A shorter reaction time would be adequate). The mixture is then filtered through a bed of diatomaceous earth. The solids are washed with chloroform, the filtrate and the washings are combined, washed with water, dried over anhydrous magnesium sulfate and evaporated to afford the crude product as a gum. From this the major component is isolated by preparative TLC (four, 2.0mm silica gel plates developed with chloroform-ethyl acetate 1:1) and identified as the title compound (487 mg). One crystallization from ethyl acetate gives 381 mg of the analytical specimen of the title compound, melting point 245°–246° C. with consistent spectral data.

Anal. Calc'd for $C_{33}H_{39}FO_5$: C, 74.13; H, 7.35; F, 3.55 Found: C, 74.37; H, 7.41; F, 3.46.

EXAMPLE 4

9-Fluoro-1',2',3',4'-tetrahydro-11β-hydroxy-3,20-dioxopregna-1,4-dieno[16α,17-b]naphthalene-21-oic acid, 1,1-dimethylethyl ester (A)

9-Fluoro-1',2',3',4'-tetrahydro-11β-hydroxy-3,20-dioxopregna-1,4-dieno[16α,17-b]naphthalene-21-oic acid A solution of 9-fluoro-1',2',3',4'-tetrahydro-11β-hydroxypregna-1,4-dieno[16α,17-b]naphthalene-21-al-3,20-dione (3.0g, see Example 1) in a mixture of dichloromethane (150 ml) and tetrahydrofuran (150 ml) containing acetic acid (3.0 ml) and water (4.0 ml) is stirred with activated manganese dioxide (6.0g) and potassium cyanide (700 mg) for 20 hours. The mixture is then filtered and the solids are washed with warm chloroform-methanol (7:3). The filtrate and the washings are combined and evaporated in vacuo. The residue is washed with water, dried, purified by chromatography, crystallized from methanol-chloroform to afford the title compound, melting point 280°–281° C. (dec.).

(B)

9-Fluoro-1',2',3',4'-tetrahydro-11β-hydroxy-3,20-dioxopregna-1,4-dieno[16α,17-b]naphthalene-21-oic acid, 1,1-dimethylethyl ester To a suspension of 9-fluoro-1',2',3',4'-tetrahydro-11β-hydroxy-3,20-dioxopregna-1,4-dieno [16α,17-b]naphthalene-21-oic acid (325 mg.) in dry dioxane (60 ml) containing sulfuric acid-phosphoric acid catalyst (0.4 ml.; prepared by the addition of the calculated amount of phosphorous pentoxide to 96% sulfuric acid to react with all of the water) in a pressure reaction vessel is passed a stream of isobutylene (until about 6 ml is added). The reaction vessel is closed and maintained at ambient temperature for 30 hours with stirring. The mixture is poured into a solution of sodium acetate hydrate (5.0g) in water (500 ml) and extracted successively with chloroform and ethyl acetate. The extracts are washed with brine, combined, dried over anhydrous magnesium sulfate and evaporated. The residue is purified by chromatography on silica gel to afford 145 mg. of the title compound, melting point 293°–296° C. (dec., discoloration starts from about 275° C.) after crystallization from acetone-hexane.

EXAMPLE 5

9-Fluoro-1',2',3',4'-tetrahydro-11β-hydroxy-3,20-dioxopregna-1,4-dieno[16α,17-b]naphthalen-21-oic acid, 2,2-dimethylpropyl ester A solution of 9-fluoro-1',2',3',4'-tetrahydro-11β-hydroxy-3,20-dioxopregna-1,4-dieno[16α,17-b]naphthalene-21-oic acid, methyl ester in dry dioxane (20 ml, distilled over sodium) and dry pyridine (15 ml) is refluxed with neopentyl alcohol (2.2 g) and sodium cyanide (100 mg) under a nitrogen atmosphere for 18 hours. The resulting solution is evaporated in vacuo and the residue is dissolved in chloroform. The chloroform solution is washed with dilute sodium chloride solution and water, dried over anhydrous sodium sulfate and evaporated in vacuo. The residue is dissolved in chloroform-hexane (9:1) and chromatographed on a 35 g-silica gel column. Elution with chloroform-hexane (9:1) gives 540 mg of material. Crystallization from acetone-hexane gives 460 mg of an analytical specimen of the title compound, melting point 329°–331° C. (dec.).

Anal. Calc'd for $C_{34}H_{41}FO_5$: C, 74.42; H, 7.53; F, 3.46. Found: C, 74.39; H, 7.73; F, 3.37.

What is claimed is:

1. A steroid having the formula

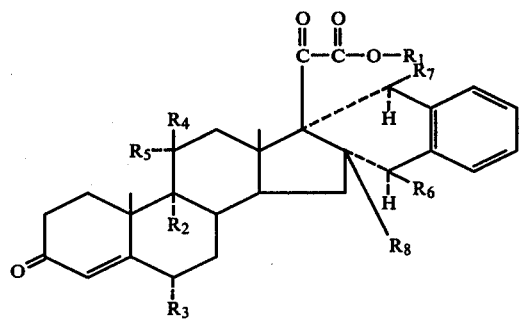

or the 1,2-dehydro derivative thereof, wherein $R_1$ is alkyl of 1 to 10 carbon atoms, aryl or arylalkyl; $R_2$ is hydrogen or halogen; $R_3$ is hydrogen, fluorine or methyl; $R_4$ is chlorine, fluorine or hydroxy and $R_5$ is hydrogen or $R_4$ and $R_5$ together are =O; $R_6$ and $R_7$ are the same or different and are hydrogen, alkyl, alkoxy, carboalkoxy, formyl,

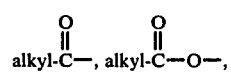

hydroxy, halogen, phenyl or cyano with the proviso that when $R_6$ and $R_7$ are different, one of $R_6$ and $R_7$ is hydrogen; $R_8$ is hydrogen or

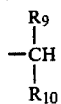

wherein $R_9$ and $R_{10}$ are the same or different and are hydrogen or alkyl.

2. A steroid in accordance with claim 1 wherein $R_1$ is alkyl of 1 to 10 carbon atoms.

3. A steroid in accordance with claim 1 wherein $R_1$ is aryl.

4. A steroild in accordance with claim 1 wherein $R_1$ is arylalkyl.

5. A steroid in accordance with claim 1 wherein $R_2$ is fluorine.

6. A steroid in accordance with claim 1 wherein $R_3$ is hydrogen.

7. A steroid in accordance with claim 1 wherein $R_4$ is hydroxy and $R_5$ is hydrogen.

8. A steroid in accordance with claim 1 wherein $R_6$ and $R_7$ are hydrogen.

9. A steroid in accordance with claim 1 wherein $R_8$ is hydrogen.

10. A steroid in accordance with claim 1 wherein $R_8$ is methyl.

11. The steroid in accordance with claim 1 having the name 9-fluoro-1',2',3',4'-tetrahydro-11β-hydroxy-3,20-dioxopregna-1,4-dieno[16α,17-b]naphthalene-21-oic acid, methyl ester.

12. The steroid in accordance with claim 1 having the name 9-fluoro-1',2',3',4'-tetrahydro-11β-hydroxy-3,20-dioxopregna-1,4-dieno[16α,17-b]naphthalen-21-oic acid, 1-methylethyl.

13. The steroid in accordance with claim 1 having the name 9-fluoro-1',2',3',4'-tetrahydro-11β-hydroxy-3,20-dioxopregna-1,4-dieno[16α,17-b]naphthalen-21-oic acid, butyl ester.

14. The steroid in accordance with claim 1 having the name 9-fluoro-1',2',3',4'-tetrahydro-11β-hydroxy-3,20-dioxopregna-1,4-dieno[16α,17-b]naphthalene-21-oic acid, 1,1-dimethylethyl ester.

15. The steroid in accordance with claim 1 having the name 9-fluoro-1',2',3',4'-tetrahydro-11β-hydroxy-3,20-dioxopregna-1,4-dieno[16α,17-b]-naphthalen-21-oic acid, 2,2-dimethylpropyl ester.

16. A steroid having the formula

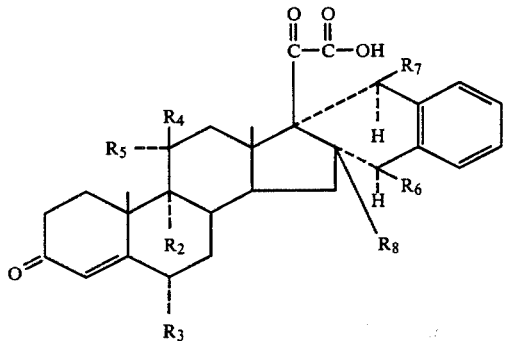

or the 1,2-dehydro derivative thereof, wherein $R_2$ is hydrogen or halogen; $R_3$ is hydrogen, fluorine or methyl; $R_4$ is chlorine, fluorine or hydroxy and $R_5$ is hydrogen or $R_4$ and $R_5$ together are =O; $R_6$ and $R_7$ are the same or different and are hydrogen, alkyl, alkoxy, carboalkoxy, formyl,

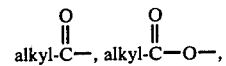

hydroxy, halogen, phenyl or cyano with the proviso that when $R_6$ and $R_7$ are different, one of $R_6$ and $R_7$ is hydrogen; $R_8$ is hydrogen or

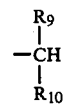

wherein $R_9$ and $R_{10}$ are the same or different and are hydrogen or alkyl.

17. A steroid having the formula

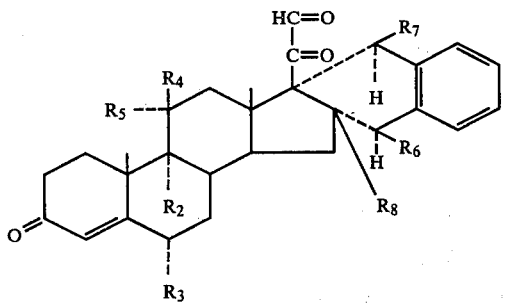

or the 1,2 dehydro derivative thereof, wherein $R_2$ is hydrogen or halogen; $R_3$ is hydrogen, fluorine or methyl; $R_4$ is chlorine, fluorine or hydroxy and $R_5$ is hydrogen or $R_4$ and $R_5$ together are =O; $R_6$ and $R_7$ are the same or different and are hydrogen, alkyl, alkoxy, carboalkoxy, formyl,

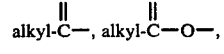

hydroxy, halogen, phenyl or cyano with the proviso that when $R_6$ and $R_7$ are different, one of $R_6$ and $R_7$ is hydrogen; $R_8$ is hydrogen or

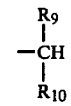

wherein $R_9$ and $R_{10}$ are the same or different and are hydrogen or alkyl.

18. A steroid having the formula

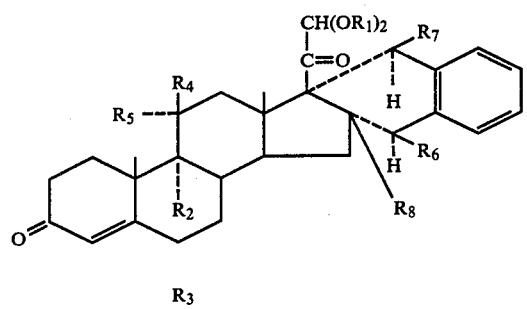

or the 1,2-dehydro derivative thereof, wherein $R_1$ is alkyl of 1 to 10 carbon atoms, aryl or arylalkyl; $R_2$ is hydrogen or halogen; $R_3$ is hydrogen, fluorine or methyl; $R_4$ is chlorine, fluorine or hydroxy and $R_5$ is hydrogen or $R_4$ and $R_5$ together are $=O$; $R_6$ and $R_7$ are the same or different and are hydrogen, alkyl, alkoxy, carboalkoxy, formyl,

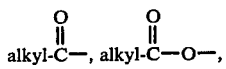

hydroxy, halogen, phenyl or cyano with the proviso that when $R_6$ and $R_7$ are different, one of $R_6$ and $R_7$ is hydrogen; $R_8$ is hydrogen or

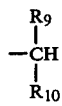

wherein $R_9$ and $R_{10}$ are the same or different and are hydrogen or alkyl.

19. A steroid having the formula

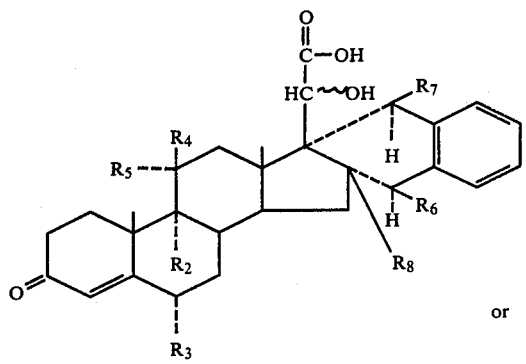

or

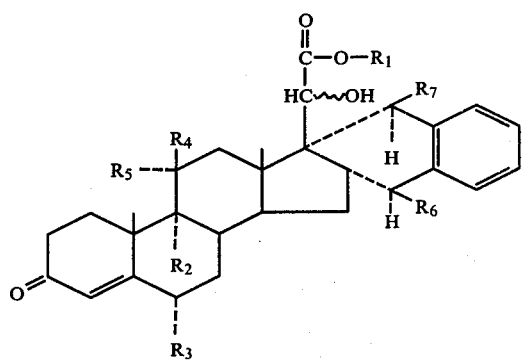

or the 1,2-dehydro derivative thereof, wherein $R_1$ is alkyl of 1 to 10 carbon atoms, aryl or arylalkyl; $R_2$ is hydrogen or halogen; $R_3$ is hydrogen, fluorine or methyl; $R_4$ is chlorine, fluorine or hydroxy and $R_5$ is hydrogen or $R_4$ and $R_5$ together are $=O$; $R_6$ and $R_7$ are the same or different and are hydrogen, alkyl, alkoxy, carboalkoxy, formyl,

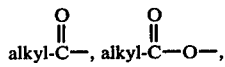

hydroxy, halogen, phenyl or cyano with the proviso that when $R_6$ and $R_7$ are different, one of $R_6$ and $R_7$ is hydrogen; $R_8$ is hydrogen or

wherein $R_9$ and $R_{10}$ are the same or different and are hydrogen or alkyl.

* * * * *

UNITED STATES PATENT OFFICE
CERTIFICATE OF CORRECTION

Patent No. 4,164,504             Dated  August 14, 1979

Inventor(s) Ravi K. Varma

It is certified that error appears in the above-identified patent and that said Letters Patent are hereby corrected as shown below:

The first structure in the "Abstract" should read:

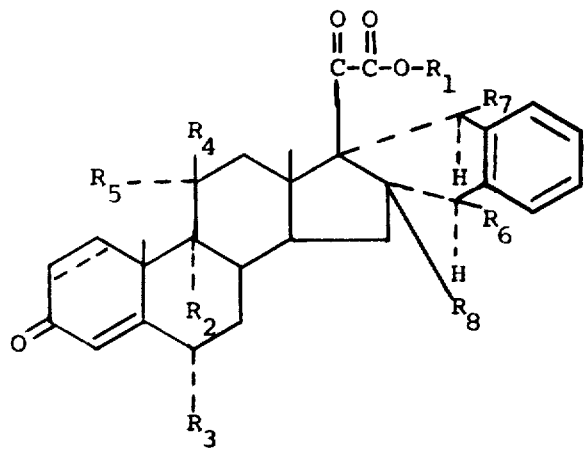

UNITED STATES PATENT OFFICE
CERTIFICATE OF CORRECTION

Patent No. 4,164,504                     Dated August 14, 1979

Inventor(s) Ravi K. Varma

It is certified that error appears in the above-identified patent and that said Letters Patent are hereby corrected as shown below:

The third structure in column 3 should read:

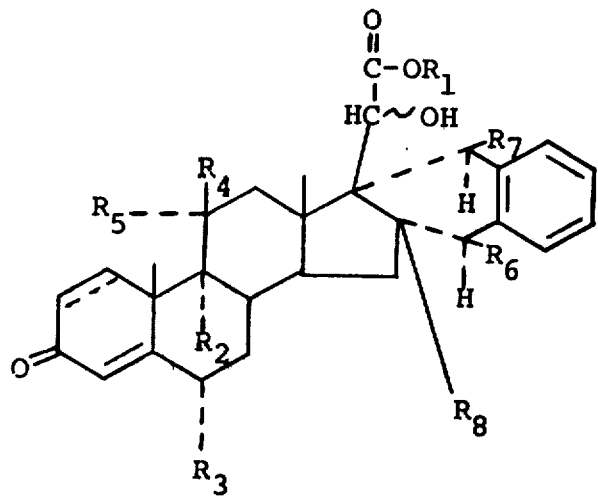

UNITED STATES PATENT OFFICE
CERTIFICATE OF CORRECTION

Patent No. 4,164,504  Dated August 14, 1979

Inventor(s) Ravi K. Varma

It is certified that error appears in the above-identified patent and that said Letters Patent are hereby corrected as shown below:

The first structure in column 4 should read:

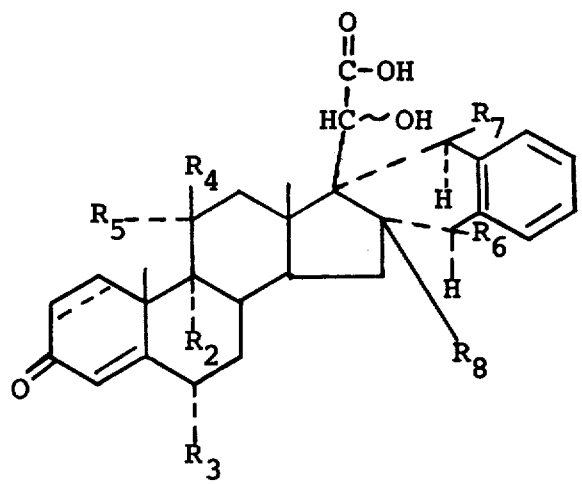

UNITED STATES PATENT OFFICE
CERTIFICATE OF CORRECTION

Patent No. 4,164,504   Dated August 14, 1979

Inventor(s) Ravi K. Varma

It is certified that error appears in the above-identified patent and that said Letters Patent are hereby corrected as shown below:

The first structure in column 11 should read:

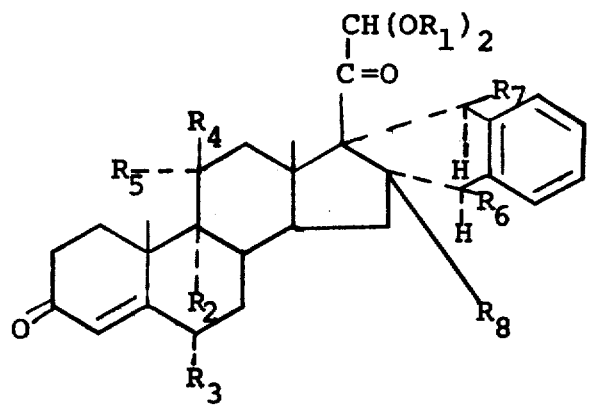

UNITED STATES PATENT OFFICE
CERTIFICATE OF CORRECTION

Patent No. 4,164,504    Dated August 14, 1979

Inventor(s) Ravi K. Varma

It is certified that error appears in the above-identified patent and that said Letters Patent are hereby corrected as shown below:

The second structure in column 12 should read:

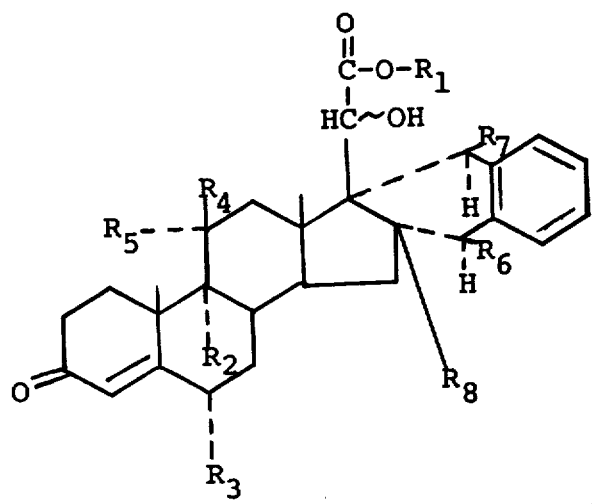

Signed and Sealed this

Tenth Day of June 1980

[SEAL]

Attest:

Attesting Officer

SIDNEY A. DIAMOND
Commissioner of Patents and Trademarks